United States Patent
Nussel et al.

(10) Patent No.: US 9,395,351 B2
(45) Date of Patent: Jul. 19, 2016

(54) SOLAR GLASS ANGLE OF INCIDENCE REFLECTANCE

(71) Applicants: Barbara Nussel, Oakland, CA (US); Richard Perkins, San Jose, CA (US)

(72) Inventors: Barbara Nussel, Oakland, CA (US); Richard Perkins, San Jose, CA (US)

(73) Assignee: SunPower Corporation, San Jose, CA (US)

( * ) Notice: Subject to any disclaimer, the term of this patent is extended or adjusted under 35 U.S.C. 154(b) by 258 days.

(21) Appl. No.: 14/107,986

(22) Filed: Dec. 16, 2013

(65) Prior Publication Data

US 2015/0168298 A1 Jun. 18, 2015

(51) Int. Cl.
| | |
|---|---|
| *G01N 21/00* | (2006.01) |
| *G02F 1/01* | (2006.01) |
| *G02F 1/13* | (2006.01) |
| *G02B 5/08* | (2006.01) |
| *G01N 33/38* | (2006.01) |
| *G01N 21/57* | (2006.01) |

(52) U.S. Cl.
CPC ............... *G01N 33/386* (2013.01); *G01N 21/57* (2013.01); *Y02E 10/52* (2013.01)

(58) Field of Classification Search
CPC .......... G01N 21/8806; G01N 21/9501; G01N 21/55; G01N 21/33; G01N 33/386; G01N 2201/061

USPC ............. 356/239.2, 239.1, 630, 237.2, 237.3, 356/445; 250/559.36; 438/7; 118/712; 136/256; 324/501, 750.12, 761.01; 257/E21.53
See application file for complete search history.

(56) References Cited

U.S. PATENT DOCUMENTS

| | | | |
|---|---|---|---|
| 8,084,550 B2 | 12/2011 | Ellington et al. | |
| 8,118,225 B2 | 2/2012 | Redmann et al. | |
| 2011/0267697 A1 | 11/2011 | Kohli et al. | |
| 2011/0276166 A1* | 11/2011 | Atanasoff | G01B 11/0625 700/104 |
| 2013/0115720 A1* | 5/2013 | Allenic | H01L 22/12 438/7 |

FOREIGN PATENT DOCUMENTS

DE 03305284 8/1984

OTHER PUBLICATIONS

Tu, Joy et al., "Critical Parameters to Investigate the Appearance Deviation for Anti-Reflection Glass PV Module," 28th European Photovoltaic Solar Energy Conference and Exhibition, Paris, Oct. 2013, 4 pages.

* cited by examiner

*Primary Examiner* — Tarifur Chowdhury
*Assistant Examiner* — Sunghee Y Gray
(74) *Attorney, Agent, or Firm* — Blakely Sokoloff Taylor Zafman LLP

(57) ABSTRACT

Reflectance measurements indicative of light reflecting relative to solar module glass can be received. It can be determined whether the reflectance measurements are within tolerance for the solar module glass.

15 Claims, 12 Drawing Sheets

SOLAR GLASS ANGLE OF INCIDENCE REFLECTANCE

BACKGROUND

In a typical solar module configuration, multiple solar cells are connected together in a single photovoltaic laminate and are covered by a layer of glass. Color variations in anti-reflective (AR) coating on the glass under certain light conditions can result in unacceptable appearance differences from one solar module to another (e.g., ranging from light grey to dark black or blue). FIGS. 1A and 1B are illustrative examples of non-uniform appearance of solar modules. As shown in both FIGS. 1A and 1B, some of the modules have a different visual appearance than nearby modules.

DETAILED DESCRIPTION

Figure 1A:
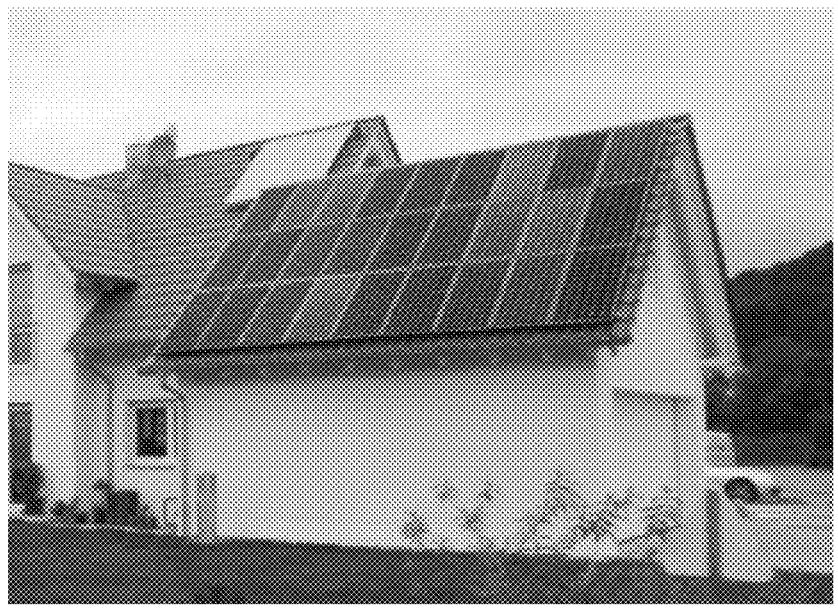
FIGS. 1A and 1B illustrate examples of non-uniform appearance of solar glass.
Figure 1B:
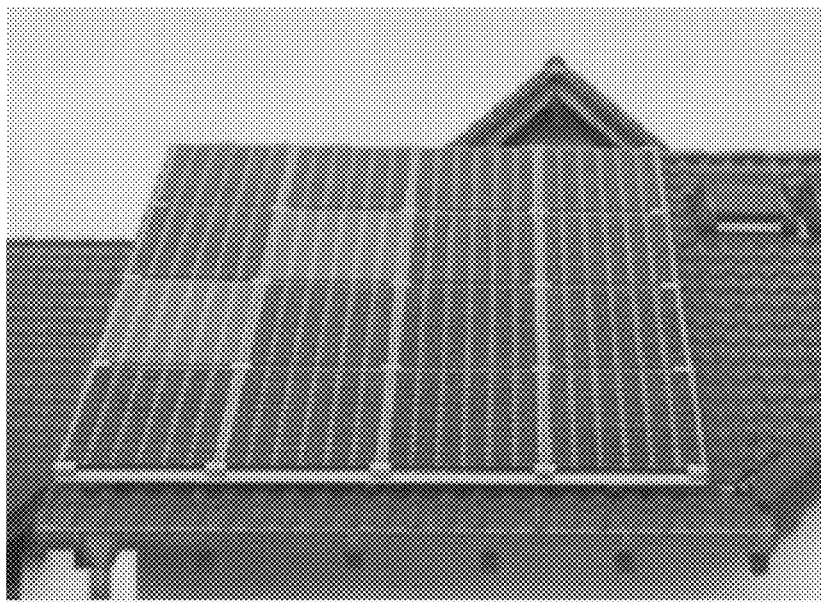

The following detailed description is merely illustrative in nature and is not intended to limit the embodiments of the subject matter of the application or uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

This specification includes references to "one embodiment" or "an embodiment." The appearances of the phrases "in one embodiment" or "in an embodiment" do not necessarily refer to the same embodiment. Particular features, structures, or characteristics may be combined in any suitable manner consistent with this disclosure.

Terminology. The following paragraphs provide definitions and/or context for terms found in this disclosure (including the appended claims):

"Gloss." This term has its ordinary and accepted meaning in the art and is used herein as a measure of the proportion of light that has a specular reflectance from a surface.

"Computer System." This term has its ordinary and accepted meaning in the art, and includes one or more computing devices operating together and any software stored thereon. A computing device includes one or more processor units and a memory subsystem. A memory subsystem may store program instructions executable by the one or more processor units. An exemplary computer system is described in more detail below and is illustrated in the Figures.

"Processor unit." This term includes any circuitry that is configured to execute program instructions (e.g., a central processing unit (CPU)). As used herein, a "processor unit" may refer to a computer subsystem having one or more processors. A processor may have one or more processing "cores" on a single die. A processor unit may be distributed across multiple dies.

"Comprising." This term is open-ended. As used in the appended claims, this term does not foreclose additional structure or steps.

"Configured To." Various units or components may be described or claimed as "configured to" perform a task or tasks. In such contexts, "configured to" is used to connote structure by indicating that the units/components include structure that performs those task or tasks during operation. As such, the unit/component can be said to be configured to perform the task even when the specified unit/component is not currently operational (e.g., is not on/active). Reciting that a unit/circuit/component is "configured to" perform one or more tasks is expressly intended not to invoke 35 U.S.C. §112, sixth paragraph, for that unit/component.

"First," "Second," etc. As used herein, these terms are used as labels for nouns that they precede, and do not imply any type of ordering (e.g., spatial, temporal, logical, etc.). For example, reference to a "first" reflectance measurement does not necessarily imply that this reflectance measurement is the first reflectance measurement in a sequence; instead the term "first" is used to differentiate this reflectance measurement from another reflectance measurement (e.g., a "second" reflectance measurement).

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

"Coupled"—The following description refers to elements or nodes or features being "coupled" together. As used herein, unless expressly stated otherwise, "coupled" means that one element/node/feature is directly or indirectly joined to (or directly or indirectly communicates with) another element/node/feature, and not necessarily mechanically.

In addition, certain terminology may also be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import.

Although much of the disclosure is described in terms of assessing uniform appearance of solar glass, the disclosed techniques and structures apply in other applications as well (e.g., assessing appearance of glass or anti-reflective (AR)

coatings generally, assessing performance of a solar module, assessing soiling and/or degradation of solar glass/AR coating, etc.).

In the following description, numerous specific details are set forth, such as specific operations, in order to provide a thorough understanding of embodiments of the present disclosure. It will be apparent to one skilled in the art that embodiments of the present disclosure may be practiced without these specific details. In other instances, well-known techniques are not described in detail in order to not unnecessarily obscure embodiments of the present disclosure.

This specification first describes an example method for determining whether reflectance measurements of a surface (e.g., solar glass) are within tolerance, followed by various examples and test data. The specification then includes a description of an example computer system, and computer-readable storage medium configured to implement the disclosed techniques. Various examples are provided throughout.

Figure 2:
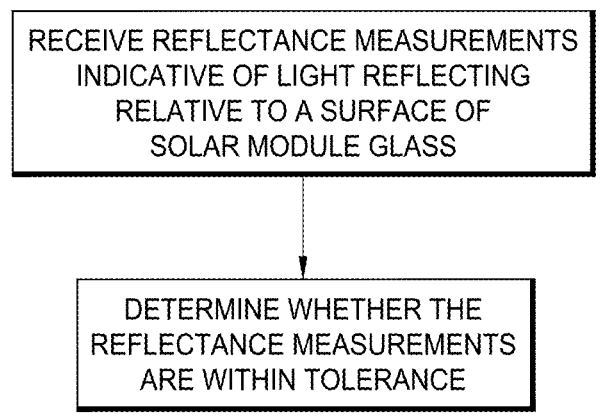
FIG. 2 is a flowchart illustrating an example method of determining whether angle of reflectance measurements are within a tolerance, according to one embodiment.

Turning now to FIG. 2, a flow chart illustrating a method for determining visual uniformity of solar glass is shown, according to some embodiments. In various embodiments, the method of FIG. 2 can include additional (or fewer) blocks than illustrated.

Figure 6:
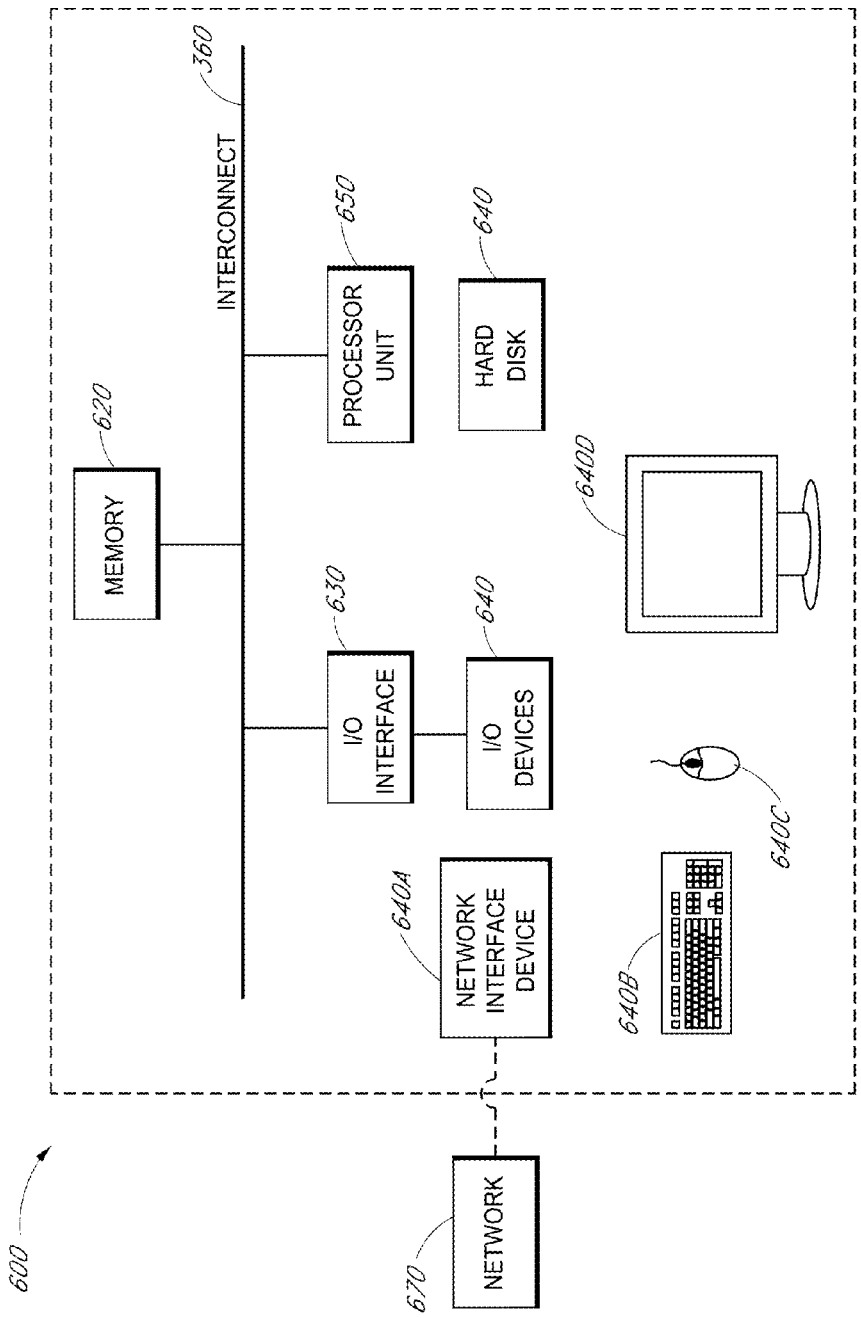
FIG. 6 illustrates an example computer system configured to implement the disclosed techniques, according to various embodiments.

As shown at 202, one or more reflectance measurements can be received, for example by computer system 600 of FIG. 6. In one embodiment, the reflectance measures are indicative of light reflecting relative to a surface of solar module glass. As used herein, solar module glass refers to the outermost (sunny-side) layer of a solar module. Note that although this description refers to solar module glass, the material may actually be something other than glass but is still suitable to be the outermost layer of the solar module. Moreover, the solar glass referred to herein does not necessarily already have to be assembled as part of a solar module. Thus, in one embodiment, solar glass can refer to a sheet of glass as raw material that can be later assembled as part of a solar module. In some embodiments, the reflectance measurements can be made prior to installing the glass as part of a module, can be made several years after the module is installed in the field, or some point in time between, among other examples.

In some embodiments, the reflectance measurements can include specular reflectance measurements (e.g., gloss measurements) that can be made at multiple angles of incidence (AOI) (e.g., 20, 60, and 85 degrees). Such reflectance measurements are referred to herein as gloss. In some embodiments, the reflectance measurements can include specular reflectance across a broad wavelength range (e.g., 300-1250 nm) at multiple angles (e.g., multiple angles between 0 and 67 degrees). Such specular reflectance across a broad wavelength range is referred to herein as AOI Rx. In some embodiments, the reflectance measurements can include total (diffuse and specular) reflectance measurements. The total reflectance measurements can include reflectance across a broad wavelength range (e.g., 300-1250 nm) at a single angle of incidence (e.g., 0 degrees). Such total reflectance measurement is referred to herein as Rx. In some embodiments, transmission measurements (e.g., specular and diffuse parts of transmission Tx) can also be received.

In various embodiments, the reflectance measurements can be received from a tool configured to generate those measurements. For example, in one embodiment, the measurements can be generated by a glossmeter, and/or a UV/Vis spectrophotometer with one or more lamps as sources, one or more types of detectors, and/or other special accessories (e.g., a universal reflectance accessory (URA)). In one embodiment, the method of FIG. 2 can include measuring the reflectance in addition to or instead of receiving the reflectance measurements. For example, the spectrophotometer can measure the reflectance and provide the data to a computer system, which can receive the data and further process the data to determine whether the data is within tolerance as described herein.

In various embodiments, each of multiple reflectance measurements can be made at a corresponding different particular angle to the surface. For example, a first reflectance measurement can be made at 85 degrees, a second reflectance measurement at 60 degrees, and a third reflectance measurement can be made at 20 degrees. In other examples, other angles (e.g., 8 degrees, 15 degrees, etc.) and/or a different number of reflectance measurements (other than three) can be used. For instance, depending on the application (e.g., performance impact, degradation, visual appearance, determining whether glass has AR coating, etc.), the angle and number of reflectance measurements may vary.

Figure 3A:
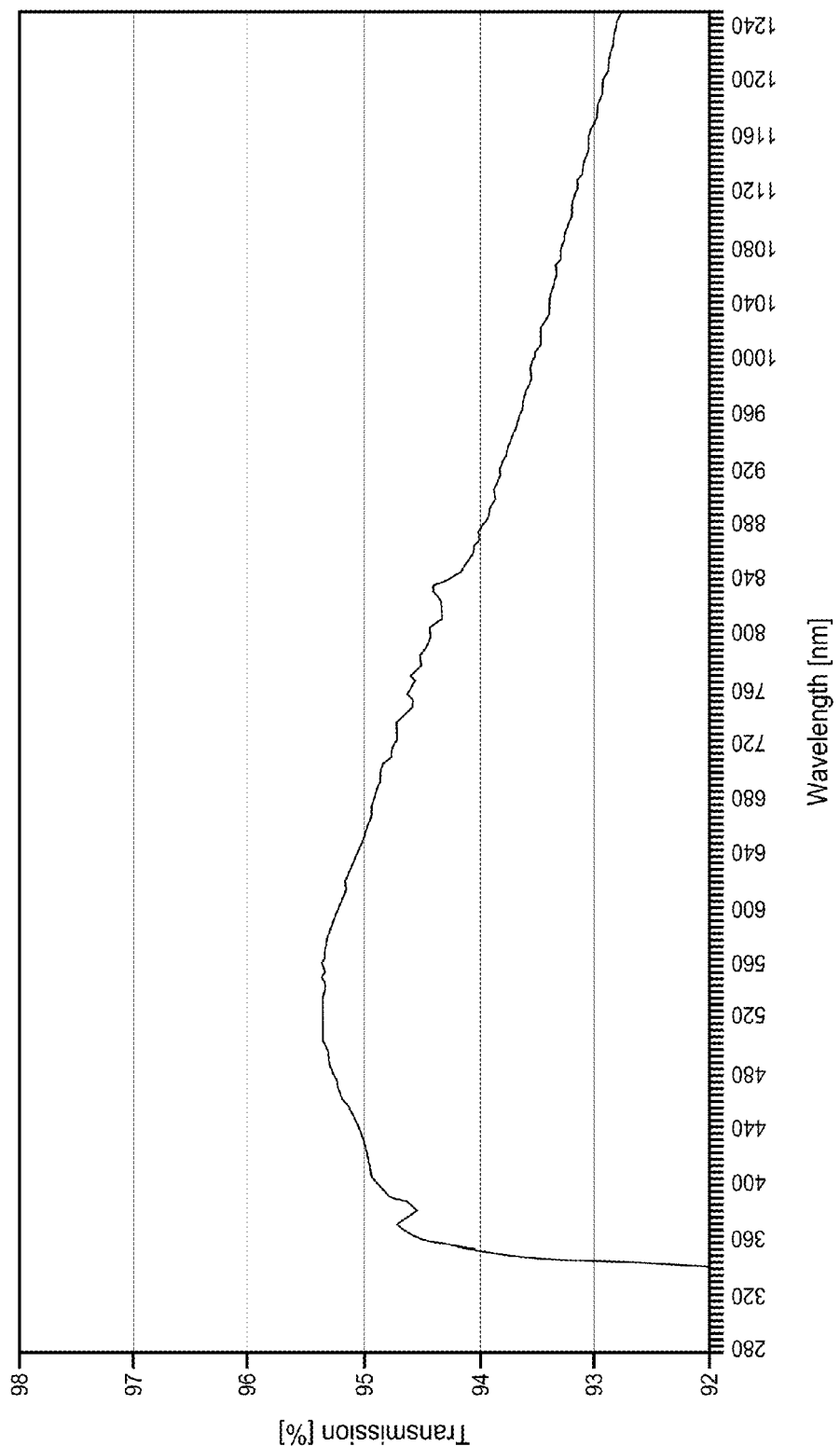
FIG. 3A illustrates an example transmission curve of a high efficiency anti-reflective coated solar glass.

FIG. 3A illustrates an example transmission curve of a high efficiency AR coated solar glass. Specifically, the transmission curve of FIG. 3A illustrates the transmission (as a percentage) relative to the wavelength in nanometers. The example AR coating used in the example corresponding to FIG. 3A shows a very high transmission in the range of 400 nm to 700 nm.

Figure 3B:
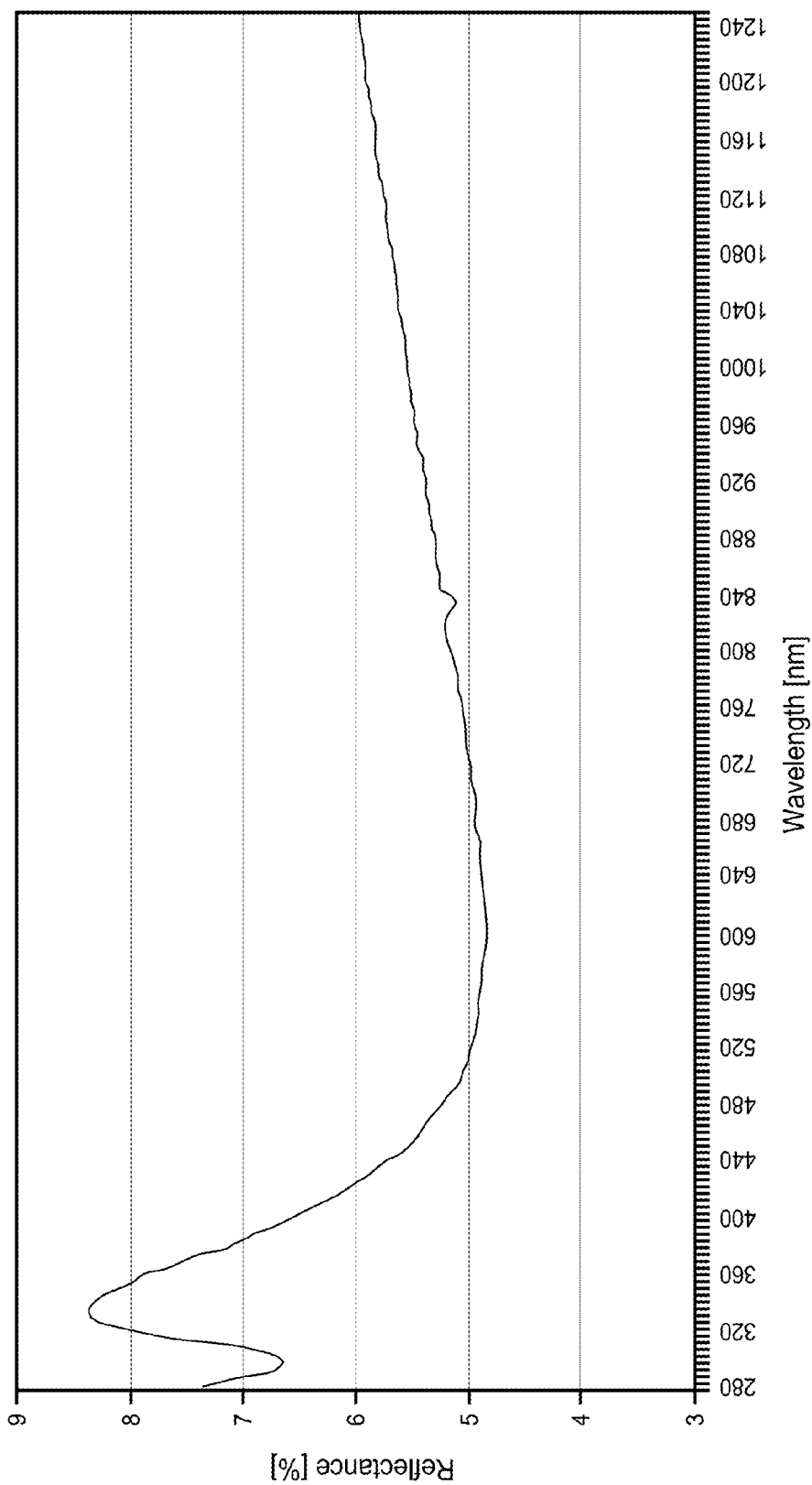
FIG. 3B illustrates an example curve of total reflectivity for a high efficiency anti-reflective coated solar glass.

FIG. 3B illustrates an example curve of total reflectivity that corresponds to the same high-efficiency AR coated solar glass for which transmission is shown in FIG. 3A. Specifically, the total reflectivity curve illustrates the reflectance (as a percentage) versus wavelength in nanometers. As shown, the example AR coating shows a large dip in the 400 nm to 700 nm wavelength range. In various embodiments, the wavelength at which the minimum of the dip of the reflectance curve occurs can determine the color appearance of the AR coating. Because AR coatings for solar panels are designed for high collection efficiency during the entire day (and therefore for various sun angles), the AR coating should be effective for various angles of light incidence.

Figure 3C:
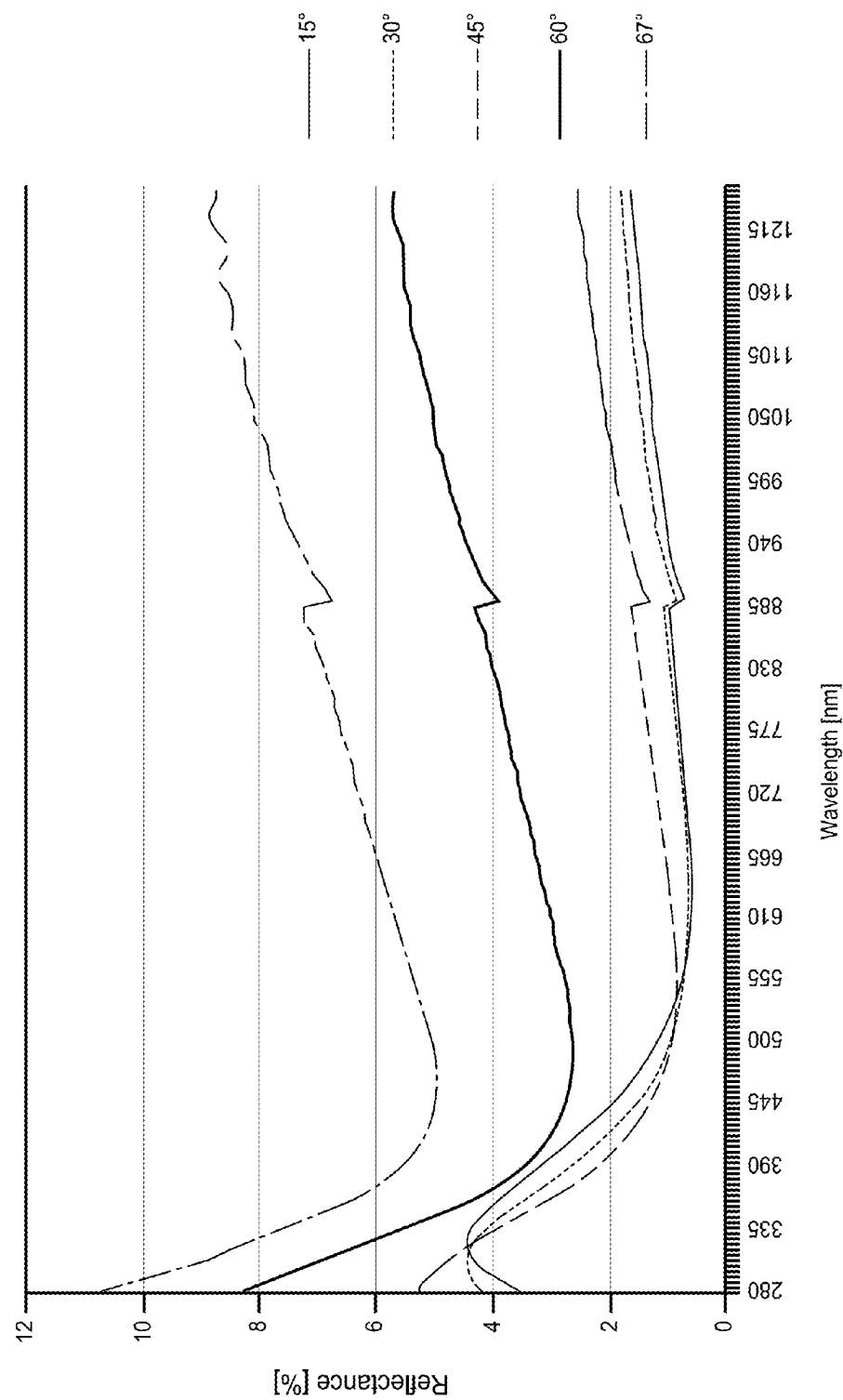
FIGS. 3C-3D illustrate example angle-of-incidence reflectance curves for high efficiency anti-reflective coated solar glass.

FIG. 3C illustrates an example of how the minimum of the reflectance shifts depending on the AOI of the light (e.g., 15, 30, 45, 60, and 67 degrees in the example curves illustrated). For instance, in the example 67 degree curve of FIG. 3C, the minimum is around 430 nm whereas in the example 15 degree curve, the minimum is around 625 nm. The shift in the reflectance minimum can translate to a shift in color appearance depending on the lighting conditions.

Figure 3D:
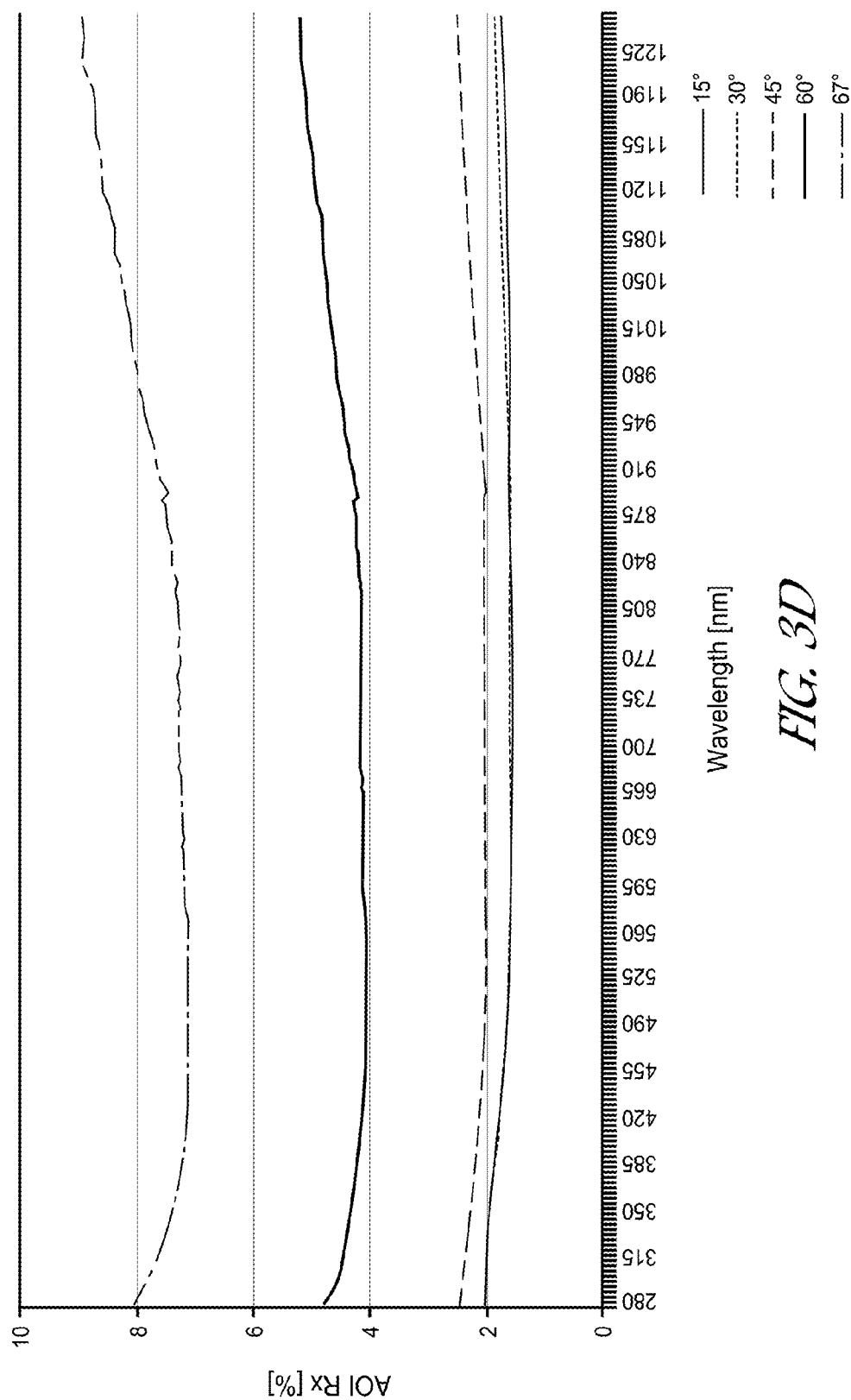

FIG. 3D illustrates example AOI reflectance curves for high efficiency AR coated solar glass that maintains a low reflection value across a wide wavelength range as well as for various angles of incidence. At the same time, the curves of FIG. 3D illustrate reflectance curves that are substantially flat across the wavelength range of 300 nm to 1200 nm. In one embodiment, curves that are substantially flat across the wavelength range of 300 nm to 1200 nm are defined as curves that have a $sd_w$ (defined below) of less than 0.2. Note that other wavelength ranges (e.g., 350 nm to 1150 nm) and parameters other than $sd_w$ can be used in other embodiments, for example, depending on tolerances and requirements.

Turning back to FIG. 2, as shown at 204, it can be determined whether the reflectance measurements are within tolerance. As described herein, whether the measurements are within tolerance can be indicative of a variety of things and is not limited to determining visual uniformity. For example, determining whether the measurements are within tolerance can be indicative of whether glass has an AR coating or not, whether appearance is substantially uniform (e.g., whether the appearance is uniform enough that the human eye does not distinguish the difference in appearance), whether performance exceeds a minimum performance threshold, whether the solar glass is soiled or has degraded, etc.

In one embodiment, it may be determined whether each reflectance measurement is within its own respective tolerance range. Moreover, in one embodiment, a respective tolerance range corresponding to the reflectance measurement made at one angle can be different than the respective tolerance range corresponding to the reflectance measurement made at another angle. For example, in one embodiment, the tolerance range for the 20 degree measurement can be +/−1-2 gloss units (GU) (e.g., 1 GU), the tolerance range for the 60 degree reflectance measurement may be +/−2-3 GU (e.g., 2 GU) and the tolerance range for the 85 degree reflectance measurement may be +/−3-4 GU (e.g., 3 GU).

In one embodiment, the tolerance range at 60 degrees can be +/−8 GU to ensure uniformity of appearance because the human eye can detect a variation of 8-10 GU at 60 degrees.

In one embodiment, a respective tolerance range corresponding to the reflectance measurement made at one angle may be the same as the respective tolerance range corresponding to the reflectance measurement made at another angle. For example, the tolerance ranges for both the 60 and 85 degree reflectance measurements may be +/−2-3 GU.

In one embodiment, the respective tolerance range corresponding to the reflectance measurement made at one angle may be variable dependent at least upon the reflectance measurement made at another angle (e.g., whether it is within its respective tolerance range, based on the absolute measurement, etc.). Accordingly, a tolerance range for a given angle may be based on a reflectance measurement made at another angle. For example, consider a scenario in which default tolerance ranges for the 60 and 85 degree measurements are +/−3 GU and +/−4 GU, respectively. If the 85 degree measurement is outside of its respective tolerance range (e.g., above 4 GU) or outside it by a certain amount/percentage (e.g., 25% above the tolerance—above 5 GU in this example), then the 60 degree tolerance range may be a lower tolerance range (e.g., to +/−1 GU) than the default 60 degree tolerance range of +/−3 GU. As another example, if the 85 degree measurement is close to 0 GU and therefore well within the tolerance range, the 60 degree tolerance range may be expanded to a broader range (e.g., +/−5 GU) than the default range.

In one embodiment, determining whether the reflectance measurements are within tolerance can include determining whether the reflectance measurements are substantially flat across a wavelength in the range of approximately 300 to 1250 nanometers. For example, in one embodiment, determining whether the reflectance measurements are substantially flat may apply to the total reflectance (diffuse plus specular). In one embodiment, such a determination may be performed in addition to determining whether the specular reflectance (gloss) is within respective tolerances at various angles. As used herein, substantially flat across a wavelength range means that variation of the curve stays within a certain percentage (e.g., within 2%) of the curve's midpoint between its minimum and maximum. For example, as shown in FIG. 3D, the 67 degree curve is has a midpoint between its minimum and maximum of approximately 8% with a minimum around 7% and a maximum around 9%. Therefore, the 67 degree curve is substantially flat across the wavelength range because the 8% value stays within a lower bound of 6% and an upper bound of 10%.

In one embodiment, determining whether the reflectance measurements are within tolerance can include determining whether a curve of the reflectance measurements versus wavelength includes a dip in the visible spectrum (e.g., approximately 400 to 700 nanometers). In one embodiment, if the curve has a dip in the visible spectrum, then the reflectance measurements are not within tolerance whereas if the curve does not have a dip in the visible spectrum, then the reflectance measurements are within tolerance.

In one embodiment, determining whether the reflectance measurements are within tolerance can include determining one or more spectrum weighting metrics based on the measurements. Example spectrum weights can include the spectrum of sunlight, the external quantum efficiency of the solar cells, sensitivity of the human eye, among others. In one embodiment, the measured spectra (e.g., reflectance and/or transmission measurements) can be multiplied by a weight curve and in some embodiments, the mean and standard deviation can be calculated over a range resulting in a spectrum weighting mean and spectrum weighting standard deviation. As an example, the spectrum weighting standard deviation, $sd_w$ can be calculated as:

$$sd_w = \sqrt{\frac{\sum_{i=1}^{N} w_i(x_i - \bar{x}_w)^2}{\frac{(N'-1)\sum_{i=1}^{N} w_i}{N'}}} \qquad \text{Equation (1)}$$

Where N is the number of weights in the weighting curve, $w_i$ is the $i^{th}$ weight in the weighting curve, $x_i$ is the $i^{th}$ measurement in the response, $\bar{x}_w$ is the weighted average of the response curve, and N' is the number of non-zero weights in the weighting curve.

Note that example spectrum weighting equations other than that shown in Equation (1) can be used in other embodiments. Similar to the gloss range examples above, in one embodiment, if the weighted deviation metric is less than a threshold value, then the reflectance measurements are within tolerance.

The weighted deviation metric can provide a variety of information. For example, a low spectrum weighting metric mean can be indicative of good flash power. As another example, a small change in the spectrum weighting mean versus angle of incidence can be indicative of good energy harvest. As yet another example, a large visible weighted standard deviation can be indicative of non-uniform color versus viewing angle and therefore indicate that the solar glass and reflectance measurements are not within tolerance.

In various embodiments, measurements made at different angles can provide complementary information. For example, gloss measured at 60 degrees and 85 degrees can be used to differentiate between non-AR glass and AR-coated glass. For prismatic/matte patterned non-AR glass, the gloss at 60 degrees may be equal or higher than the gloss at 85 degrees. For prismatic/matte patterned solar glass with an AR coating, the gloss at 60 degrees can be 10 GU lower than the gloss at 85 degrees. Therefore, by using such information, it can be determined whether solar glass is within tolerance (e.g., whether the solar glass is AR-coated).

As another example of the complementary information, for a prismatic/matte patterned solar glass with AR coating, a gloss measurement at 85 degrees (supplemented by the gloss measurement at 60 degrees) can provide information on the base glass used. It can thus be an indicator of a change in the base glass manufacturing process, such as glass from a different furnace, different patterning line, change in patterning roller, or age of the patterning roller, among other changes.

In one embodiment, gloss measured at 60 degrees is directly correlated to the thickness of the AR coating for prismatic/matte patterned AR solar glass. The thicker the AR coating, the lower the gloss is at 60 degrees. The gloss of the base glass can influence the gloss of the AR-coated glass. Given the same AR coating technology, coating thickness, and supplier, any variation in base glass gloss can result in a gloss variation of the AR-coated glass.

In one embodiment, if the gloss of the base glass (before AR coating) and the gloss of the AR-coated glass is known at the time of manufacturing the PV modules, gloss measurements made at 60 and 85 degrees can be used to determine the grade of degradation of the AR coating over time.

In one embodiment, the method of FIG. 2 can include generating the curve(s) of reflectance measurements versus wavelength and providing the curve for display.

Determining whether reflectance measurements are within tolerance can be used in a variety of manners. For example, based on whether the reflectance measurements are within tolerance, it may be determined whether solar module glass is within a visual appearance tolerance (e.g., substantially uniform appearance). The tolerance determination can be used to determine whether the glass includes an AR coating or not, to monitor consistency of base glass before it goes into an AR-coating process, to monitor batch-to-batch consistency in appearance of AR-glass, to detect variation in AR coating thickness, and/or to measure/determine soiling and/or degradation of installed solar modules, among other examples.

The techniques disclosed herein can help ensure consistency in appearance between adjacent panels. For example, AR-glass from different batches, from different factories, and/or from different suppliers can potentially be used in a single installation (e.g., on the same roof) without visible appearance differences to the human eye. Thus, in one embodiment, the techniques used herein can be used to establish a specification to define the AR coating process. The techniques described herein can also be used to control AR coating thickness, detect changes in the base glass (e.g., different furnace, different manufacturing conditions (e.g., pull speed, temperature, etc.), a different backside pattern (e.g., age of pattern roller, etc.), etc.), control consistency of manufacturing processes, use as a tool in root cause analysis of module appearance differences in the field, among other uses.

Figure 4A:
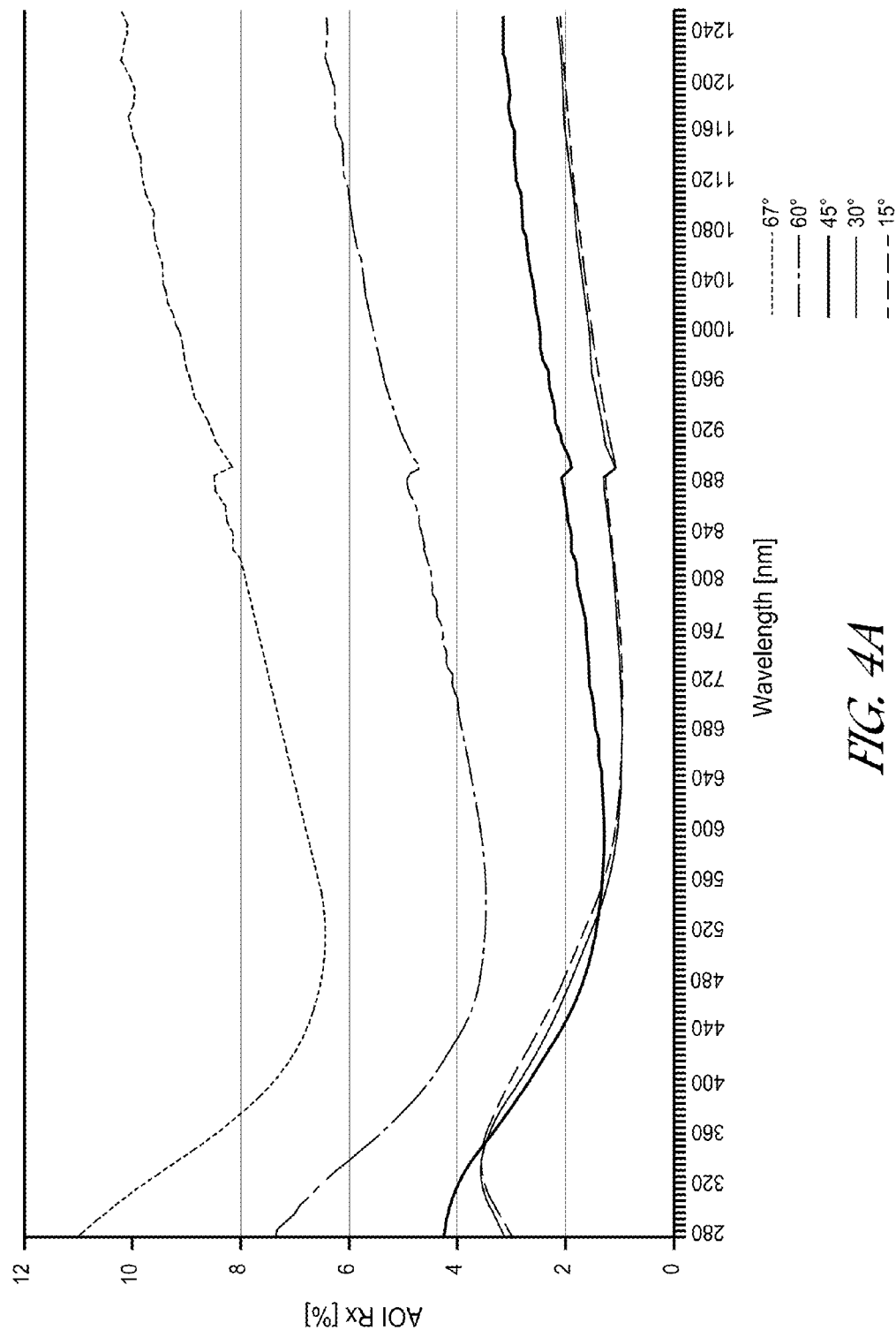
FIGS. 4A-4D illustrate example curves of total reflectivity for high efficiency anti-reflective coated solar glass.
Figure 4B:
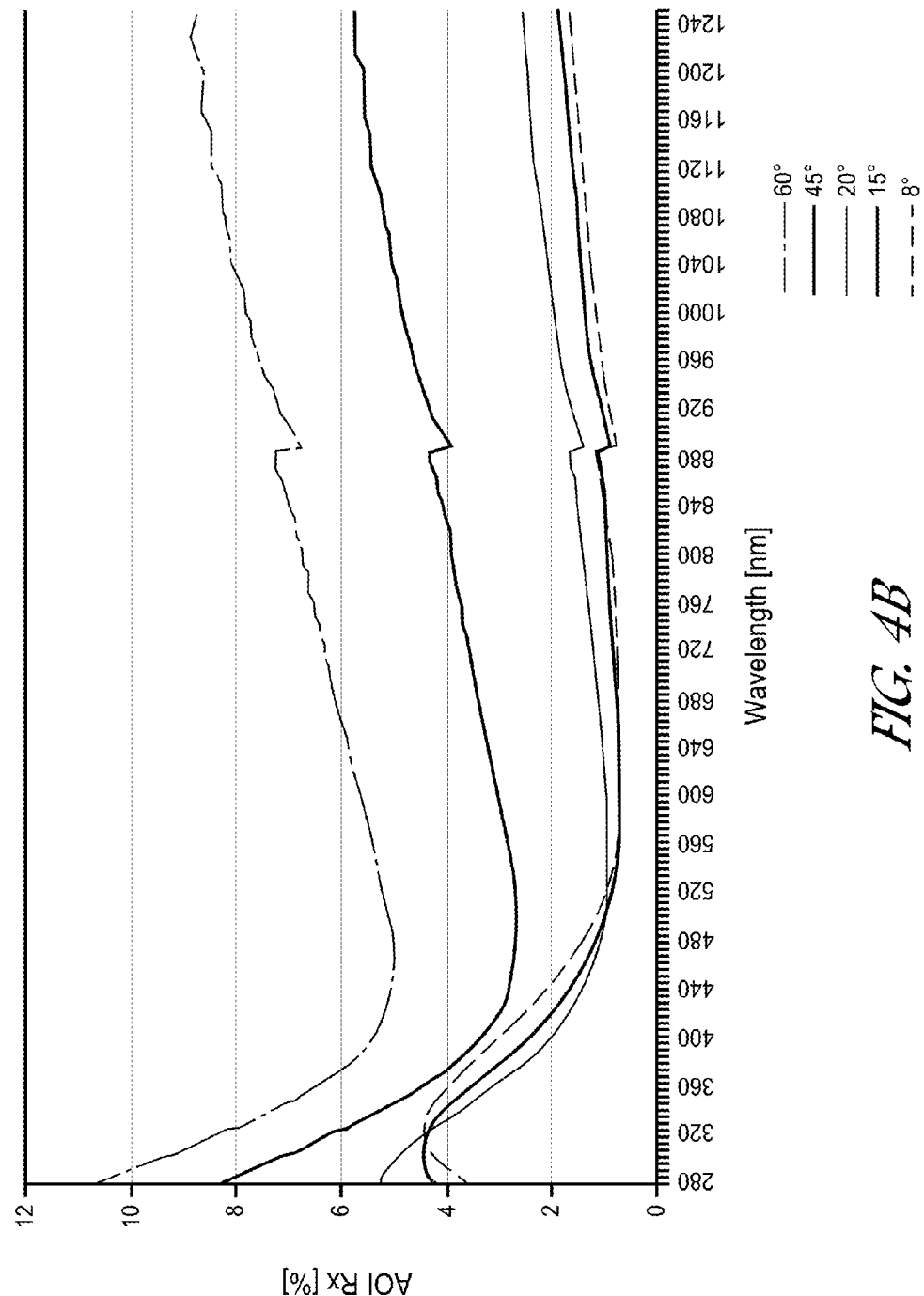
Figure 4C:
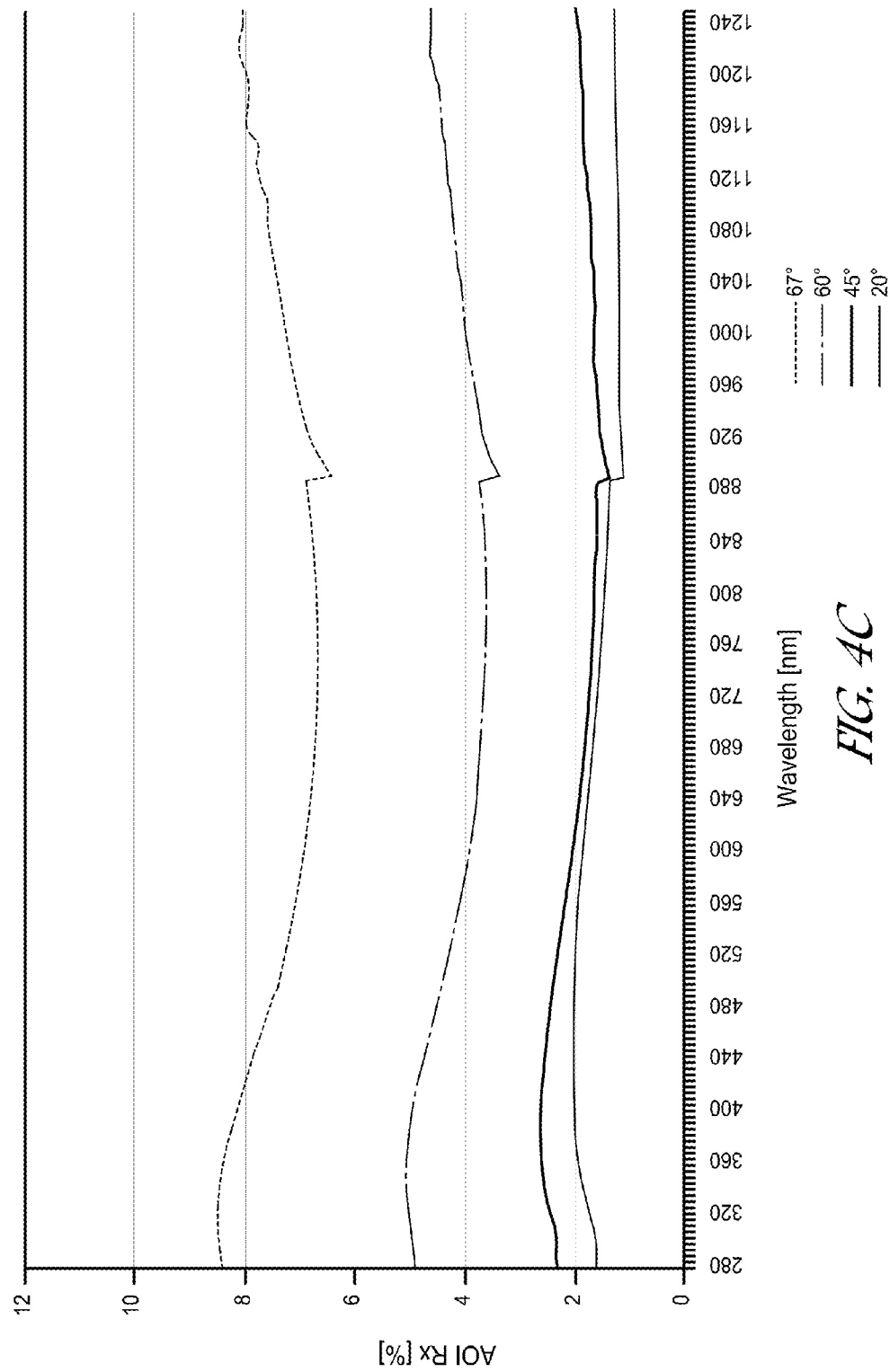
Figure 4D:
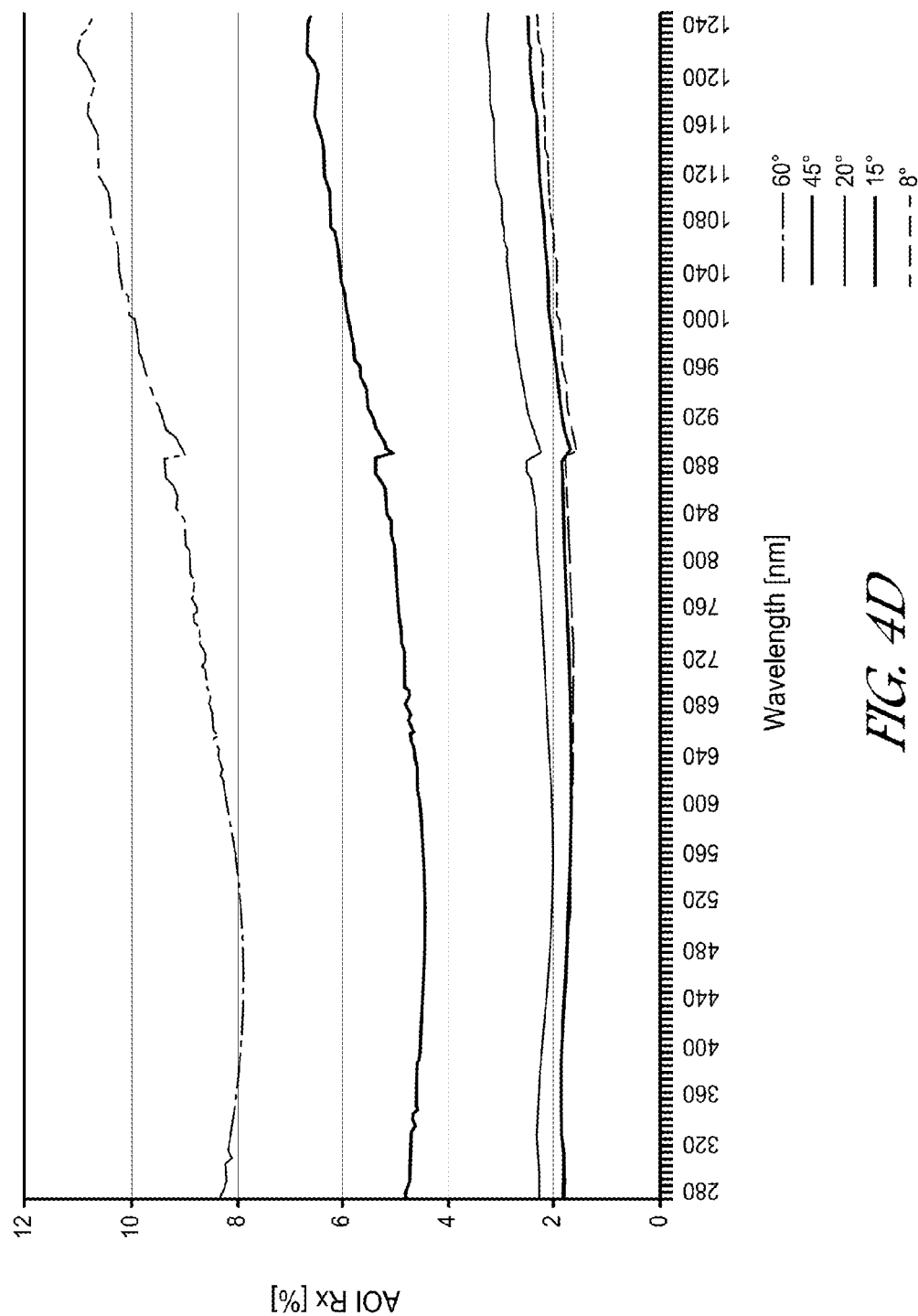

FIGS. 4A-4D illustrate example curves of AOI-dependent reflectance for high efficiency AR-coated solar glass. The curves of FIGS. 4A and 4B illustrate deep dips in the reflectance curves with minimums that include large shifts. The AR-coated solar glass corresponding to those curves would not show uniform appearance. In contrast, the curves of FIGS. 4C and 4D are substantially flat across approximately 300 nm to 1250 nm and do not include a dip in the visible spectrum (e.g., approximately 400 nm to 700 nm). As used herein, a curve does not include a dip in the visible spectrum if the curve does not include a dip greater than 1-1.5% reflectance. As there is no pronounced dip in the curves of FIGS. 4C and 4D, the change in color appearance for such AR-coated glass would be much less pronounced than the AR-coated glass corresponding to FIGS. 4A and 4B.

Figure 5:
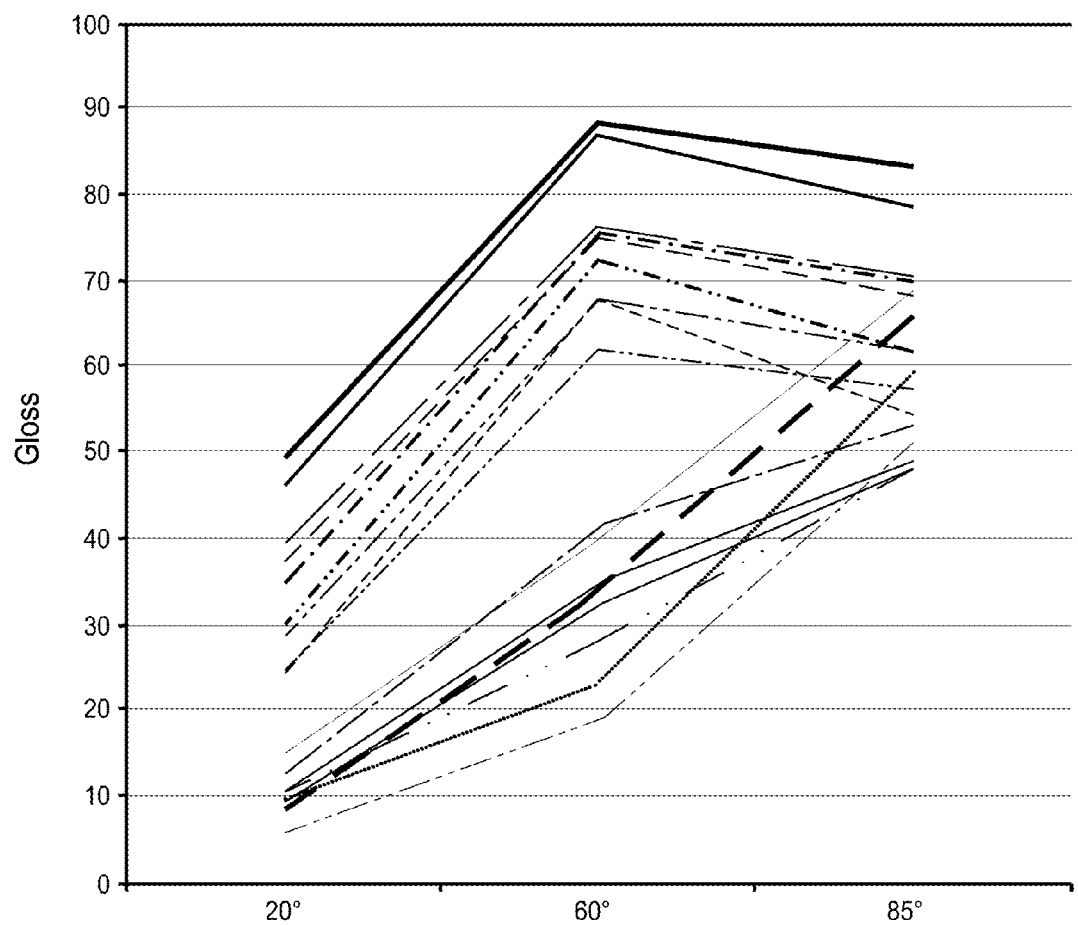
FIG. 5 illustrates example gloss curves for high efficiency anti-reflective coated solar glass.

FIG. 5 illustrates example gloss curves for high efficiency solar glass. FIG. 5 illustrates the stark difference in gloss at 60 degrees for AR-coated glass versus non-AR-coated (NAR) glass. As shown, the upper 9 curves in FIG. 5 correspond to NAR glass where the gloss at 60 degrees is higher than the gloss at 85 degrees. The remaining curves correspond to AR glass where the gloss at 60 degrees is lower than the gloss at 85 degrees. In various embodiments, the determination of whether the reflectance measurements are within tolerance can include a determination of whether the glass is AR coated or not.

Turning now to FIG. 6, an example computer system 600 configured to implement the disclosed techniques is shown. Computer system 600 can be any suitable device, including, but not limited to a personal computer system, desktop computer, laptop or notebook computer, mainframe computer system, server farm, web server, handheld computer or tablet device, workstation, network computer, mobile device, etc. Computer system 600 can also be any type of network peripheral device such as a storage device, switch, modem, router, etc. Although a single computer system 600 is shown in FIG. 6 for convenience, system 600 can also be implemented as two or more computer systems operating together.

As shown, computer system 600 includes a processor unit 650, memory 620, input/output (I/O) interface 630 coupled via an interconnect 660 (e.g., a system bus). I/O interface 630 is coupled to one or more I/O devices 640.

In various embodiments, processor unit 650 can include one or more processors. In some embodiments, processor unit 650 can include one or more coprocessor units. In some embodiments, multiple instances of processor unit 650 can be coupled to interconnect 660. Processor unit 650 (or each processor within 650) can contain a cache or other form of on-board memory. In general computer system 600 is not limited to any particular type of processor unit or processor subsystem.

Memory 620 is usable by processor unit 650 (e.g., to store instructions executable by and data used by unit 650). Memory 620 may be implemented by any suitable type of physical memory media, including hard disk storage, floppy disk storage, removable disk storage, flash memory, random access memory (RAM—SRAM, EDO RAM, SDRAM, DDR SDRAM, Rambus® RAM, etc.), ROM (PROM, EEPROM, etc.), and so on. Memory 620 may consist solely of volatile memory in one embodiment.

Memory in computer system 600 is not necessarily limited to memory 620. Rather, computer system 600 may be said to have a "memory subsystem" that includes various types/locations of memory. For example, the memory subsystem of computer system 600 may, in one embodiment, include memory 620, cache memory in processor unit 650, storage on I/O devices 640 (e.g., a hard drive, storage array, etc.), and so on. Accordingly, the phrase "memory subsystem" is representative of various types of possible memory media within computer system 600. The memory subsystem of computer 600 may store program instructions executable by processor unit 650, including program instructions executable to implement the various techniques disclosed herein.

I/O interface 630 may represent one or more interfaces and may be any of various types of interfaces configured to couple to and communicate with other devices, according to various embodiments. In one embodiment, I/O interface 630 is a bridge chip from a front-side to one or more back-side buses. I/O interface 630 may be coupled to one or more I/O devices 640 via one or more corresponding buses or other interfaces. Examples of I/O devices include storage devices (hard disk (e.g., 640E), optical drive, removable flash drive, storage array, SAN, or an associated controller), network interface devices (e.g., 640A, which may couple to a local or wide-area network), user interface devices (e.g., mouse 640B, keyboard 640C, display monitor 640D) or other devices (e.g., graphics, sound, etc.). In one embodiment, computer system 600 is coupled to a network 670 via a network interface device 640A. I/O devices 640 are not limited to the examples listed above. All depicted I/O devices 640 need not be present in all embodiments of computer system 600.

Computer system 600 (or multiple instances of computer system 600) may be used to implement the various techniques described herein. Articles of manufacture that store instructions (and, optionally, data) executable by a computer system to implement various techniques disclosed herein are also contemplated. These articles of manufacture include tangible computer-readable memory media. The contemplated tangible computer-readable memory media include portions of the memory subsystem of computer system 600 (without limitation SDRAM, DDR SDRAM, RDRAM, SRAM, flash memory, and various types of ROM, etc.), as well as storage media or memory media such as magnetic (e.g., disk) or optical media (e.g., CD, DVD, and related technologies, etc.). The tangible computer-readable memory media may be either volatile or nonvolatile memory.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

What is claimed is:

1. A method for determining visual uniformity of solar module glass, comprising:
   receiving a plurality of reflectance measurements indicative of light reflecting relative to a surface of the solar module glass, wherein each of the plurality of reflectance measurements is made at a corresponding different particular angle to the surface; determining whether the plurality of reflectance measurements are within respective tolerance ranges corresponding to a reflectance ranges for the solar module glass; and determining a first of the respective tolerance ranges for a reflectance measurement made at a first angle to the surface based on a second of the reflectance measurements made at a second angle to the surface.

2. The method of claim 1, wherein said receiving the plurality of reflectance measurements includes receiving a plurality of specular reflectance measurements, wherein said determining includes determining whether the plurality of specular reflectance measurements are within the respective tolerance ranges.

3. The method of claim 1, wherein said receiving the plurality of reflectance measurements includes receiving a plurality of diffuse and specular reflectance measurements, wherein said determining includes determining whether the plurality of diffuse and specular reflectance measurements are within the respective tolerance ranges.

4. The method of claim 1, wherein said receiving a plurality of reflectance measurements includes receiving a respective reflectance measurement made at 20 degrees, 60 degrees, and 85 degrees.

5. The method of claim 1, wherein said determining includes determining whether the plurality of reflectance measurements are within respective tolerance ranges, wherein a first one of the respective tolerance ranges is different than a second one of the respective tolerance ranges.

6. The method of claim 1, said determining the first tolerance range is based on the second reflectance measurement being outside of a second of the respective tolerance ranges.

7. The method of claim 1, further comprising:
   determining whether the solar module glass includes an anti-reflective coating based on at least one of the reflectance measurement.

8. The method of claim 1, wherein said determining includes determining whether the reflectance measurements are substantially flat across a wavelength in the range of approximately 300 nanometers to 1250 nanometers.

9. The method of claim 1, wherein said determining includes determining whether a curve of the plurality of reflectance measurements versus wavelength includes a dip in a wavelength of approximately 400 nm to 700 nm.

10. The method of claim 1, wherein said determining is based on a weighted deviation metric applied to the plurality of reflectance measurements.

11. A method for determining visual uniformity of solar module glass, comprising:
    receiving a first reflectance measurement indicative of light reflectance from a glass solar module surface at a first angle relative to the glass solar module surface;
    receiving a second reflectance measurement indicative of light reflectance from the glass solar module surface at a second angle relative to the glass solar module surface;
    determining, based on the first and second reflectance measurements, whether the solar module glass is within a respective tolerance range corresponding to a reflectance range for the solar module glass; determining whether the first reflectance measurement is within a first tolerance range; and determining whether the second reflectance measurement is within a second, different tolerance range; and determining the second tolerance range based on the first reflectance measurement.

12. The method of claim 11, wherein said determining whether a curve of the first and second reflectance measurements versus wavelength includes a dip in a wavelength of approximately 400 nm to 700 nm.

13. A non-transitory computer-readable storage medium storing program instructions executable by a computing device to:
    receive a first reflectance measurement indicative of light reflectance from a glass solar module surface at a first angle relative to the glass solar module surface;
    receive a second reflectance measurement indicative of light reflectance from the glass solar module surface at a second angle relative to the glass solar module surface;
    determine whether the first and second reflectance measurements are within tolerance ranges corresponding to reflectance ranges for the glass solar module surface;
    determining whether the first reflectance measurement is within a first tolerance range; and determining whether the second reflectance measurement is within a second tolerance range which is a different tolerance range from the first tolerance range and determine the second tolerance range based on the first reflectance measurement relative to the first tolerance range.

14. The non-transitory computer-readable storage medium of claim 13, wherein the program instructions are further executable by the computing device to:
- receive a third reflectance measurement indicative of light reflectance from the glass solar module surface at a third angle relative to the surface; and
- determining whether the third reflectance measurement is within tolerance.

15. The non-transitory computer-readable storage medium of claim 13, wherein the program instructions are further executable by the computing device to:
- generate a curve of the first and second reflectance measurements versus wavelength.

* * * * *